(12) United States Patent
Aldawsari et al.

(10) Patent No.: US 11,058,637 B1
(45) Date of Patent: Jul. 13, 2021

(54) SURFACE-MODIFIED EMULSOMES FOR INTRANASAL DELIVERY OF DRUGS

(71) Applicant: King Abdulaziz University, Jeddah (SA)

(72) Inventors: Hibah M. Aldawsari, Jeddah (SA); Shaimaa M. Badr-Eldin, Jeddah (SA); Nourah Y. Assiri, Jeddah (SA); Abdelsattar Omar, Jeddah (SA)

(73) Assignee: King Abdulaziz University, Jeddah (SA)

( * ) Notice: Subject to any disclaimer, the term of this patent is extended or adjusted under 35 U.S.C. 154(b) by 0 days.

(21) Appl. No.: 17/104,055

(22) Filed: Nov. 25, 2020

(51) Int. Cl.
*A61K 9/127* (2006.01)
*A61K 31/475* (2006.01)
*A61K 31/4375* (2006.01)
*A61K 9/00* (2006.01)

(52) U.S. Cl.
CPC .......... *A61K 9/1273* (2013.01); *A61K 9/0043* (2013.01); *A61K 31/475* (2013.01)

(58) Field of Classification Search
CPC .. A61K 9/1273; A61K 31/475; A61K 9/0043; A61K 9/127; A61K 9/1271; A61K 9/1272; A61K 9/1274; A61K 31/4375
See application file for complete search history.

(56) References Cited

U.S. PATENT DOCUMENTS

| | | | | |
|---|---|---|---|---|
| 4,035,370 A * | 7/1977 | Lorincz | ............... | C07D 461/00 546/51 |
| 4,882,336 A * | 11/1989 | Tigyi | ............... | A61P 37/00 514/283 |
| 5,013,556 A * | 5/1991 | Woodie | ............... | A61P 35/00 424/450 |
| 5,213,804 A * | 5/1993 | Martin | ............... | A61K 9/1271 424/450 |
| 5,576,016 A * | 11/1996 | Amselem | ............... | A61K 9/5123 424/450 |
| 2005/0175683 A1 * | 8/2005 | Zhang | ............... | A61K 31/70 424/450 |
| 2007/0116753 A1 * | 5/2007 | Hong | ............... | A61P 43/00 424/450 |
| 2015/0086484 A1 * | 3/2015 | Hanes | ............... | A61K 31/704 424/9.3 |
| 2016/0228364 A1 * | 8/2016 | Rafalko | ............... | A61K 9/1271 |
| 2017/0281541 A1 * | 10/2017 | Yu | ............... | A61K 9/1271 |

OTHER PUBLICATIONS

Nair, Aswathy S., et al. "Emulsomes: a novel liposomal formulation for sustained drug delivery." International Research Journal of Pharmaceutical and Applied Sciences 3.5 (2013): 192-196.*
Vyas, S. P., Rasika Subhedar, and Sanyog Jain. "Development and characterization of emulsomes for sustained and targeted delivery of an antiviral agent to liver." Journal of Pharmacy and Pharmacology 58.3 (2006): 321-326.*
Bhana, Nila, et al. "Zidovudine." Pediatric Drugs 4.8 (2002): 515-553.*
El-Zaafarany, Ghada M., et al. "Identifying lipidic emulsomes for improved oxcarbazepine brain targeting: In vitro and rat in vivo studies." International journal of pharmaceutics 503.1-2 (2016): 127-140.*
Nasr, Maha, and Sara A. Wahdan. "Neuroprotective effects of novel nanosystems simultaneously loaded with vinpocetine and piracetam after intranasal administration." Life sciences 226 (2019): 117-129.*
Gill B, Singh J, Sharma V, Hah Kumar SL. Emulsomes: An emerging vesicular drug delivery system. Asian J Pharm 2012;6:87-94.*
H Ucisik, Mehmet, Uwe B Sleytr, and Bernhard Schuster. "Emulsomes meet S-layer proteins: an emerging targeted drug delivery system." Current pharmaceutical biotechnology 16.4 (2015): 392-405.*

* cited by examiner

*Primary Examiner* — Bethany P Barham
*Assistant Examiner* — Peter Anthopolos
(74) *Attorney, Agent, or Firm* — W & C IP (57) ABSTRACT

Emulsome compositions comprising phosphatidylcholine, cholesterol, tristearin, and one or more lipophilic bioactive agents such as vinpocetine are provided. The emulsomes may further comprise surface modifications of either [N-(carbonyl-methoxypropylethyleneglycol-2000)-1,2-distearoyl-sn-glycero-3-phosphoethanolamine, sodium salt] (MPEG-DSPE) for peglyation or stearylamine for cationization. Methods of improving brain delivery of lipophilic bioactive agents by intranasally administering such emulsome compositions are also provided.

4 Claims, 6 Drawing Sheets

SURFACE-MODIFIED EMULSOMES FOR INTRANASAL DELIVERY OF DRUGS

BACKGROUND OF THE INVENTION

Field of the Invention

The disclosure relates to improved surface-modified emulsome compositions and methods for utilizing such emulsomes for intranasal delivery of poorly water-soluble bioactive agents in a subject.

Background

The blood-brain barrier (BBB) efficiently protects the central nervous system (CNS) from pathogens, toxins, and external agents by limiting influx of molecules and ions and restricting transcellular transports of more than 95% of potential drug substances[1]. This strong barrier capacity of BBB limits therapeutic treatments to cross over in sufficient quantities to achieve the necessary efficacy in the brain and therefore poses difficulties in treating CNS disorders e.g. brain tumors, neurodegeneration, stroke, and cerebral ischemia. Recent advances in strategies to bypass the BBB by utilizing alternative administration methods, such as intranasal administration which takes benefit of olfactory and trigeminal-associated extracellular pathways connection to the CNS, provide painless and non-invasive alternative routes to deliver therapeutic agents into the brain[2]. However, despite numerous advantages such as rapid onset of action and minimized systemic exposure, nose-to-brain delivery methods have significant drawbacks. For example, high clearance of the drugs due to enzymatic degradations and small absorption surface in the nasal cavity often hinder effective and direct drug delivery. Therefore, there is a need in the art for improved formulation compositions for intranasal delivery of therapeutic agents to the brain.

SUMMARY

Features and advantages of the present disclosure will be set forth in the description of disclosure that follows, and in part will be apparent from the description of may be learned by practice of the disclosure. The disclosure will be realized and attained by the compositions and methods particularly pointed out in the written description and claims hereof.

The disclosure provides compositions of emulsomes comprising phosphatidylcholine, cholesterol, and tristearin. The emulsomes may further comprise surface modifications of either [N-(carbonyl-methoxypropylethyleneglycol-2000)-1, 2-distearoyl-sn-glycero-3-phosphoethanolamine, sodium salt] (MPEG-DSPE) for peglyation or stearylamine for cationization. The surface modifications as contemplated in this disclosure have several advantages including: 1) providing much higher drug entrapment and more controlled drug release than do comparable emulsomes that lack the specific surface modifications and 2) resulting more efficient lipophilic drug delivery to the brain than do non-modified emulsomes and orally administered marketed tablets.

In another aspect, the disclosure provides methods for delivering a lipophilic agent to a subject via intranasal administration of the compositions as described herein. In particular, the disclosure provides an exemplary lipophilic agent, Vinpocetine (VIN), which is encapsulated in the surface-modified emulsomes described herein for its intranasal delivery to the CNS.

DETAILED DESCRIPTION

The disclosure provides advances in the manufacture of surface-modified emulsomes comprising novel compositions; and the method of brain delivery of lipophilic agents encapsulated within said emulsomes.

As used herein, the term "emulsomes" means nanoemulsions of particles comprising solid fat cores stabilized by phospholipid (PL) envelope at the aqueous interface forming a bilayer. The internal core of emulsomes is composed of lipid that exhibits a solid or liquid crystal physical condition. In one embodiment of the disclosure, emulsomes are first formulated by using techniques commonly known for emulsomes and/or liposomes production, examples of which include but are not limited to the thin-film hydration technique and cast film technique[3]. The general method to prepare said emulsomes is to dissolve Phospholipids (PL) Lipoid S 100 (Phosphatidylcholine from soya), Cholesterol (CH) and any one of solid lipids (SL) such as Tristeararin (TS) or Tripalmitin (TP), together or separately in varying concentrations, in volatile solvents such as dichloromethane, chloroform or methanol. Following the evaporation of the solvents, the resulting products are collected, dried in a rotary evaporator at about 30 to 50° C., re-hydrated with gentle agitation in an aqueous solution, e.g. 10 mM Phosphate buffer (pH 6.8) for 1 hr at 20 to 30° C., and ultrasonicated to yield nanoemulsions at amplitude 40%, 750 W, 20 kHz for 2 minutes in 2 cycles with 5 minutes between each cycle.

In some embodiments, the ratio of phosphatidylcholine to solid lipid is from 2:1 to 4:1, e.g. 2.5:1 to 1.5:1, e.g. 3:1. In some embodiments, the ratio of phosphatidylcholine to cholesterol is from 3:1 to 1:1, e.g. 2.5:1 to 1.5:1, e.g. 2:1.

In one embodiment, the surface of emulsomes is modified with cationic charge inducer stearylamine (SA), wherein the concentration of SA lies in the range of from about 0.2 M to 0.8 M, or even in the range of from 0.3 M to about 0.7 M, i.e. about 0.1, 0.2, 0.3, 0.4, 0.5, 0.6, 0.7, 0.8 M. Alternative surface modifier may be used such as [N-(carbonyl-methoxypropylethyleneglycol-2000)-1,2-distearoyl-sn-glycero-3-phosphoethanolamine, sodium salt] (MPEG-DSPE) with concentration in the range of from about 0.1 M to about 0.3 M, i.e. about 0.1, 0.2, or 0.3 M. All of the surface-modifier (SM) reactions described herein are prepared using a similar method. The surface-modified emulsomes comprising of different surface-modifier—SA or MPEG-DSPE—may be prepared by combining with varying concentrations or ratios of the emulsome components, for example, as presented in Table 1.

TABLE 1

Compositions of surface-modified emulsomes in phosphate buffer pH 6.8.

| Run | PL:SL | PL:CH | SL | SM | SM Conc. |
|---|---|---|---|---|---|
| E19 | 3:1 | 2:1 | Tristearin | Stearylamine | 0.25 M |
| E20 | 3:1 | 2:1 | Tristearin | Stearylamine | 0.5 M |
| E21 | 3:1 | 2:1 | Tristearin | Stearylamine | 0.75 M |
| E22 | 3:1 | 2:1 | Tristearin | MPEG-DSPE | 0.1 M |
| E23 | 3:1 | 2:1 | Tristearin | MPEG-DSPE | 0.2 M |
| E24 | 3:1 | 2:1 | Tristearin | MPEG-DSPE | 0.3 M |

Significantly, the one or more surface-modifications described herein on emulsomes contributes to an exceptional brain-targeted drug delivery and thus can be very useful in delivery of drugs or agents that may require alternative routes of administration which bypass blood-brain barrier (BBB) and/or for chronic treatment which may result in adverse effects from chronic systemic exposures of untargeted regions in the body. In some embodiments related to intranasal delivery, the method involves: 1) identification of a subject in need of intranasal delivery for central nervous system (CNS) disorders e.g. brain tumors, neurodegeneration, stroke, or cerebral ischemia; 2) generation of cationic modified or PEGylated emulsomes with encapsulation of one or more lipophilic or poorly water-soluble bioactive agents; and 3) intranasal instillation or other forms of intranasal administration of emulsome-encapsulated said agent(s) in the nostril of a subject. As used herein, the terms "intranasal delivery" or "nose-to-brain delivery" mean delivering drugs or agents in each nostril through a tube or a catheter into the nasal cavity but also may include the use of nasal drops, sprays, squeeze bottles, and metered dose nebulizers.

As used herein, the term "subject" denotes a mammal, such as rodent, a feline, a canine, a primate, and a human.

As used herein, the term "lipophilic agents" are defined as "poorly water-soluble agents" and the two terms are interchangeably used in the disclosure. As used herein, the term "poorly water-soluble" refers to having a solubility in water at 20° C. of less than 1%, e.g., 0.01% (w/v), i.e., a "sparingly soluble to very slightly soluble drug" as described in Remington, *The Science and Practice of Pharmacy*, 19$^{th}$ Edition, A. R. Gennaro, Ed., Mack Publishing Company, Vol. 1, p. 195 (1995). Examples of therapeutic classes of therapeutic compounds include, but are not limited to, antihypertensives, antianxiety agents, anticlotting agents, anticonvulsants, blood glucose-lowering agents, decongestants, antihistamines, antitussives, antineoplastics, beta (β)-blockers, anti-inflammatories, antipsychotic agents, cognitive enhancers, anti-atherosclerotic agents, cholesterol reducing agents, antiobesity agents, autoimmune disorder agents, anti-impotence agents, antibacterial and antifungal agents, hypnotic agents, antibiotics, anti-depressants, anti-Parkinsonism agents, anti-Alzheimer's disease agents, antiviral agents and combinations of the foregoing. Suitable lipophilic agents include, but are not limited to, vinpocetine, rivastigmine, donepexil, risperidone, sertraline, etc.

The term "agents" refer to any synthetic and/or natural molecules but excludes biological macromoleucles (e.g., proteins, nucleic acids, etc.). Preferred lipophilic agents range in size up to about 5000 Da, more preferably up to 2000 Da, and most preferably up to about 1000 Da.

In an exemplary embodiment, the emulsome-encapsulated bioactive agent is Vinpocetine (VIN). As used herein, the term "Vinpocetine" (VIN), also known as AY-27255, Cavinton, Eburnamenine-14-carboxylic acid, Ethyl apovincaminate, Ethylapovincaminoate, Ethyl ester, RGH-4405, TCV-3b, Vinpocetin, and Vinpocetina, has its general meaning in the art as a vinca alkaloid, and some clinical implications of VIN include but not limited to improvement of cerebral blood flow, brain metabolism, memory functions and neuroprotective actions. VIN-containing emulsomes may be prepared as follows: VIN, Lipoid S 100, solid lipid (TS or TP) (3:1 ratio to Lipoid S 100), Cholesterol (2:1 ratio to Lipoid S 100), and surface modifier (SA or MPEG-DSPE) were dissolved in specified volume of chloroform/methanol mixture (2:1, v/v). The grams of VIN in said preparation can vary from about e.g. 0.1 to about 100 g (e.g. about all numbers in between) or more, e.g. tens, hundreds or thousands of grams in industrial preparations.

The VIN-containing emulsomes produced by the method described herein may be used in any of a variety of therapeutic applications, e.g. 1) they may be administered through numerous routes, examples of routes include but are not limited to intranasal, oral-route forms such as gel capsules granules or suspensions or solutions, sublingual and buccal administration forms, aerosols, implants, subcutaneous, transdermal, topical, intraperitoneal, intramuscular, intravenous, subdermal, transdermal, intrathecal, intraduodenal, and rectal administration forms, 2) they may be used as a treatment of CNS-related disorders such as acute stroke, cerebral vascular ischemia, cerebral dysfunction and Alzheimer's disease and/or used as a supplement for improving symptoms of dementia, energy metabolism, weight loss, and anti-aging.

In some embodiments, the active agent (e.g. VNP) is administered to the subject in a therapeutically effective amount. By a "therapeutically effective amount" is meant a sufficient amount of active agent to treat the disease or disorder at a reasonable benefit/risk ratio applicable to any medical treatment. It will be understood that the total daily usage of the compositions of the present invention will be decided by the attending physician within the scope of sound medical judgment. The specific therapeutically effective dose level for any particular subject will depend upon a variety of factors including the disorder being treated and the severity of the disorder; activity of the specific compound employed; the specific composition employed, the age, body weight, general health, sex and diet of the subject; the time of administration, route of administration, and rate of excretion of the specific compound employed; the duration of the treatment; drugs used in combination or coincidental with the specific active agent employed; and like factors well known in the medical arts. For example, it is well within the skill of the art to start doses of the compound at levels or frequencies lower than those required to achieve the desired therapeutic effect and to gradually increase the dosage or frequency until the desired effect is achieved.

However, the daily dosage of the active agent may be varied over a wide range from 0.01 to 1,000 mg per adult per day. In particular, the compositions contain 0.01, 0.05, 0.1, 0.5, 1.0, 2.5, 5.0, 10.0, 15.0, 25.0, 50.0, 100, 250 and 500 mg of the active ingredient for the symptomatic adjustment of the dosage to the subject to be treated. A medicament typically contains from about 0.01 mg to about 500 mg of the active ingredient, in particular from 1 mg to about 100 mg of the active ingredient. An effective amount of the drug is ordinarily supplied at a dosage level from 0.0002 mg/kg to about 20 mg/kg of body weight per day, especially from about 0.001 mg/kg to 7 mg/kg of body weight per day.

The active agent may be combined with pharmaceutically acceptable excipients. "Pharmaceutically" or "pharmaceutically acceptable" refer to molecular entities and compositions that do not produce an adverse, allergic or other untoward reaction when administered to a mammal, especially a human, as appropriate. A pharmaceutically acceptable carrier or excipient refers to a non-toxic solid, semisolid or liquid filler, diluent, encapsulating material or formulation auxiliary of any type.

In one embodiment, said VIN-emulsomes are formed with all or some composite materials comprising any said phospholipids, solid lipids (either TS or TP, preferably 3:1 ratio to Lipoid S 100 PL), Cholesterol (preferably 2:1 ratio to Lipoid S 100 PL), and surface modifiers (either SA or MPEG-DSPE) that are dissolved together with about 60 mg or less or more of VIN in any volatile solvents; and are prepared by thin-film hydration method as described herein, to be intranasally administered in the form of a pharmaceutical composition to a subject. It will be understood that the total usage of the compounds and compositions of the present disclosure will be decided by medical professionals within the scope of sound medical judgment for the specific activity of the VIN-emulsomes employed. The Vin-emulsomes may be administered intranasally in a single shot of about 0.3 to about 1 mL into nostrils using PE tube and one can readily employ other administering instruments not named but known to the art. The person responsible for administration will, in any event, determine the appropriate volume for the individual subject.

In another embodiment, the concentration of VIN in the brain following intranasal administration of said surface-modified VIN-emulsomes is determined by utilizing methods well known in the art, for example using lytic enzymes or chemical solutions to extract lysates from brain cell or brain tissue or plasma samples of a subject and calculate VIN concentration over the average weight of subject's brain (ng/g) after liquid chromatography tandem mass spectrometry (LC-MS/MS) analysis.

Before exemplary embodiments of the present disclosure are described in greater detail, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order which is logically possible.

While the disclosure has been described in terms of various embodiments, other variations of this technology will occur to those of skill in the art, and all such variations are encompassed by the disclosure. The following examples serve to further illustrate the disclosure but should not be construed as limiting the subject matter in any way.

EXAMPLES

Example 1. Characterization of the Effect of Independent Variables and Surface Modification Via Cationization and PEGylation in VIN-Emulsomes This example describes the development of surface modifications for the synthesis of brain-targeting emulsomes containing CNS pharmacological agent, VIN. The optimized VIN-emulsomes were prepared with cationic charge inducer, stearylamine (SA) and PEGylated phospholipid (MPEG-DSPE), in different molar ratios consisting of (3:1 PL:SL, 2:1 PL:CH, and TS). Different molar ratios of either SA or MPEG-DSPE were dissolved in specified volume of chloroform/methanol mixture (2:1, v/v) along with VIN, Lipoid S 100®, CH, and TS. The surface-modified optimized emulsomes were characterized for vesicle size, zeta potential, entrapment efficiency, and in vitro drug release.

The surface of the optimized VIN emulsomes (E12) was further modified by addition of different molar ratios of positive charge inducer (SA) or MPEG-DSPE to produce cationic or PEGylated emulsomes, respectively. Both SA and MPEG-DSPE were introduced aiming at improving VIN emuslomes penetration though BBB.

Adding SA leads to development of cationic emulsomes, where the positive charge surface interacts with negative charges present at the BBB, leading to adsorptive-mediated endocytosis. In addition, it enhances the penetration of drug across BBB, through enhancing the electrostatic attraction between negative BBB and positive charge of cationic emulsomes. MPEG-DSPE leads to the development of long circulating emulsomes. This effect could be credited to the steric stabilization induced by the incorporated PEGylated lipids, subsequently avoidance of opsonization and phagocytosis by hepatic and splenic reticuloendothelial system (RES) macrophages of PEGylated emulsomes[4]. Microscopic examination showed almost spherical unilamellar vesicles with uniform size for all formulations. FIG. 1 demonstrated phospholipids as bright surface surrounded solid lipid core, the bright color disappeared in FIGS. 1 (B) and (C) this may be attributed to the presence of stearylamine or MPEG-DSPE at surface of emulsomes.

The shape and morphological characteristics of optimized emulsomes were studied here using transmission electron microscope (TEM). One drop of the diluted emulsomal dispersion was applied on a carbon coated grid and left for 3 minutes to allow its adsorption on the carbon film, and the emulsomes were then stained with of phosphotungsitc acid (1% w/v). The excess stain was removed with filter paper and the grid was air-dried thoroughly before visualization. The sample was examined with 22,500× magnification (FIG. 1).

Variation in size was observed; TS based emulsomes had larger size than TP based emulsomes. The influence of the PL:SL ($X_1$), PL:CH ($X_2$), and SL type ($X_3$) on the vesicle size ($Y_1$) of VIN emulsomes is graphically illustrated as 3D-surface plots represented in FIG. 2. ANOVA showed that the PL:SL ratio ($X_1$), PL:CH ratio ($X_2$), and SL type ($X_3$), had significant effect on vesicle size. In addition, the interaction between PL:SL and PL:CH ($X_1$ $X_2$), and PL:CH and solid lipid type ($X_2$ $X_3$) were significant (P=0.0323, 0.0001 respectively). Increasing PL:CH ratio from 2:1 to 8:1 resulted in significant increase in the vesicle size. This finding could be attributed to the formation of multiple bilayers that lead to increased vesicle size.

On the other hand, the effect of cholesterol is inversely related to the vesicle size, where decreasing cholesterol ratio from 2:1 to 8:1 (PL:CH) resulted in increased vesicle size. This could be due to higher concentration of CH that resulted in increased the lipophilicity of emulsomal formulation, thus preventing water uptake across lipid bilayer causing size reduction. Regarding SL type, increasing the amount of SL is significantly increases the vesicle size of prepared emulsomes. TS based emulsomes showed larger vesicle size than TP based emulsomes. This could be probably due to the higher chain length of TS molecule than TP (FIG. 2).

Moreover, all emulsomes formulations discussed herein exhibited negative charge which showed zeta values above 30 mV indicate the kinetic stability of the vesicles with minimized aggregation. Zeta potential is indication for stability of the vesicular system. The vesicles dispersion is considered to be stable for zeta potential above 30 mV due to the electric repulsion that prevent particle aggregations. The influence of the PL:SL ($X_1$), PL:CH ($X_2$), and SL type ($X_3$) on the zeta potential ($Y_2$) of VIN emulsomes is graphically illustrated as 3D-surface plots represented in FIG. 3. The ANOVA results showed that the PL:SL, and PL:CH ratio had significant effect on ZP (P<0.0001). As illustrated in FIG. 3, increasing PL:CH ratio from 2:1 to 8:1 lead to increasing the absolute values of zeta potential. This could be ascribed to the increase of the negative anionic soya phosphatidylcholine in the outer layers. This figure also demonstrates that increasing cholesterol amount resulted in significant decrease in the value of zeta potential. However, no significant difference in zeta potential was observed between TP and TS based emulsomes (P=0.1410). This finding could be explained by presence of the solid lipid in the core of emulsomes. Accordingly, they don't contribute to the net surface charge.

Encapsulation of drug in the lipid vesicular system as emulsomes could improve its oral bioavailability, as well as control its release. The influence of the PL:SL ($X_1$), PL:CH ($X_2$), and SL type ($X_3$) on the entrapment efficiency ($Y_3$) of VIN emulsomes is graphically illustrated as 3D-surface plots represented in FIG. 4. Statistical analysis using ANOVA showed that both PL:SL, and PL:CH ratio significantly affected the entrapment efficiency of prepared emulsomes (P<0.0001). No significant difference in EE between two solid lipid types was observed (P=0.694). FIG. 4 shows that drug entrapment increases with increasing PL:CH ratio. VIN is lipophilic drug; it disperses more efficiently in high lipid concentration. Thus, PL resulted in increasing availability of more lipid to dissolve the drug with consequently increase in its entrapment. It was evident that the highest drug entrapment was observed at highest PL:CH ratio of 8:1. Regarding CH, it was found that the amount of CH augments the entrapment efficiency, since cholesterol influence the lamellar rigidity of emulsomes with subsequent stabilization of the prepared emulsomes, that leads to reduced drug leakage. The obtained results confirmed that the cholesterol increased the membrane rigidity, as well as reduced liposomal membrane permeability consequently improve drug entrapment[6]. Regarding SL type, statistical analysis reported no significant difference in EE between TS and TP, this may be due to the almost the same lipophilicity of used solid lipid; C18 for TS, C16 for TP.

Cumulative percent released and release efficiency after 24 h ($RE_{24\ h}$) from prepared VIN emulsomes were depicted in FIG. 5. All the formulations showed slow drug release within first two hours, and no burst release was observed. This could be attributed to the entrapment of lipophilic VIN inside the hydrophobic part of emulsomes bilayer, with consequent retardation of drug release. VIN was released gradually from prepared emulsomes over 24 h. Statistical analysis revealed that the significant factor affected drug release was PL:CH, followed by SL type and PL:SL (P=<0.0001, 0.0008, and 0.0018, respectively). In addition, the interaction between PL:SL and SL type ($X_1$ $X_3$), and PL:CH and SL type ($X_2$ $X_3$) were significant (P=0.0315, and 0.015, respectively). As illustrated in FIG. 5, the percent of drug release increased with increasing PL:CH ratio. This could be due to high cholesterol concentration that increases bilayer rigidity and retards the drug release. This result could be explained by the presence of cholesterol in the phospholipid bilayer that modulates membrane fluidity by limiting the movement of hydrocarbon chains, decreasing bilayer permeability and reducing efflux of the entrapped drug, resulting in retarding drug release. Additionally, increasing PL could contribute to increased VIN release. This finding could be due to bipolar nature of phospholipid which enhances drug (VIN) diffusion across lipid bilayer and accelerates its release.

Moreover, significant decrease in the percentage of VIN release after 24 h was associated with increasing the amount of solid lipid. This might be due to the solid lipid core of emulsomes that solubilize and entraps high amount of lipophilic drug (VIN). During the release process, the drug will diffuse from solid lipid core and PL bilayer which acts as a barrier resulting in slow drug release. The superiority of TS in sustaining drug release than TP is evident. TS had longer chain than TP that allow more time for VIN to diffuse from SL core to the release medium.

Desirability function was utilized to select the optimized VIN emulsomes using Design-Expert software. The optimization was based on minimizing the vesicle size and release efficiency after 24 hr, and maximizing magnitude of zeta potential and entrapment efficiency. The compositions of optimized VIN emulsomes were PL: SL (3:1), PL:CH (2:1), and SL type (TS). The optimized formulation fulfilled the requirement with desirability of 0.718. E12, whose composition includes the combination of the optimized variables, showed vesicle size of 329.50±3.54 nm, zeta potential of −48.50±4.95 mV, EE of 78.00±2.83%, and $RE_{24\ h}$ of 25.62±2.15%. Hence, E12 was chosen for further investigations.

Characterization of Cationic and PEGylated VIN Emulsomes

Vesicle size is very important for improving the transportation across the BBB, and enhancing the binding and the uptake of the emulsomes by the brain cells. Vesicle sizes of cationic VIN emulsomes were larger in size than the corresponding optimized formulation (E12). One-way ANOVA showed a significant difference in the vesicle size among the formulations E12 (optimized emulsomes), E19, E20, and E21 (cationic VIN emulsomes) (P=0.001). To identify source of variation, multiple comparison Tukey's HSD test was performed, it revealed significant difference between optimized VIN emulsomes (E12) and each of the cationic emulsomes (E19, E20, and E21), P=0.039, 0.005, and 0.001, respectively. This result confirms that addition of cationic surface charge inducer significantly increases vesicle size. However, there was no significant difference in the vesicle size upon using different concentration of SA. The significant increase in vesicle size of cationic emulsomes compared to the optimized one could be ascribed to the properties of SA solution. According to the literature, SA solution could affect the dispersibility of emulsomes due to its viscous nature, as well as, it could induce the repulsion between phospholipid bilayer. This increase in spacing is caused by pushing the polar heads of the phospholipids outwards within the multilamellar structure[7]. On the other hand, mean vesicle size of PEGylated emulsomes were less than the corresponding optimized emulsomes (E12), as shown in Table 1. ANOVA showed a significant difference in the vesicle size among the formulation E12 (optimized emulsomes), E22, E23, and E24 (PEGylated VIN emulsomes) (P=0.002). Multiple comparisons Tukey's HSD revealed significant difference between optimized VIN emulsomes (E12) and each of the PEGylated emulsomes (E22, E23, and E24), P=0.002, 0.003, and 0.012, respectively. This result confirms that addition of MPEG-DSPE significantly decreases vesicle size. However, there was no significant difference in the vesicle size upon using different concentration of MPEG-DSPE. The significant decrease in the vesicle size on addition of MPEG-DSPE might suggest the penetration of MPEG-DSPE into emulsomes bilayer, pressing them together and thus promoting the packaging of phospholipid within emulsomes bilayer.

The entire charge of optimized VIN emulsomes could be affected by the charge of SA and/or lipid MPEG-DSPE. Emulsomes exhibited positive charge in all cationic VIN emulsomes formulations. The results showed zeta values were decreased and shifted from negative to positive charge. ANOVA showed a significant difference in the zeta potential among the formulation E12 (optimized emulsomes), E19, E20, and E21 (cationic VIN emulsomes). Multiple comparison Tukey's HSD test was performed, it revealed significant difference between optimized VIN emulsomes (E12) and each of the cationic emulsomes (E19, E20, and E21). However, there was no significant difference in zeta potential between each of the cationic emulsomes. The observed effect could be attributed to the role of SA as a positive charge inducer.

Regarding PEGylated VIN emulsomes zeta potential values were less than non-PEGylated emulsomes. Regarding PEGylated VIN emulsomes, mean zeta potential were less than non-PEGylated emulsomes. ANOVA showed a significant difference in the vesicle size among the formulation E12 (optimized emulsomes), E22, E23, and E24 (PEGylated VIN emulsomes). Multiple comparisons Tukey's HSD revealed significant difference between optimized VIN emulsomes (E12) and each of the PEGylated emulsomes (E22, E23, and E24). Also, there were statistical difference in zeta potential between E22 and E24 (P=0.023). This result confirms that addition of MPEG-DSPE significantly decreases the absolute value of zeta potential. The effect of PEGylation on the zeta potential could be credited to the charge-shielding effect of polyethylene glycol (PEG) moiety.

The EE % of cationic emulsomes was higher than that of optimized emulsomes (E12). However, the difference in EE was not significant according to ANOVA analysis (P=0.623). The slight increase in the entrapment efficiency of cationic emulsomes could be attributed to the induced repulsion between phospholipid bilayer that lead to increase of the vesicle size as well as increase of the entrapping volume. It was also observed that increase SA molar concentration above 0.5 lead to reduction of VIN entrapment. At higher SA concentrations, high repulsion between phospholipid bilayer occurs leading to disruption of emulsomes structure as it lacks the amphiphilic nature of phospholipids forming unstable vesicles.

Regarding PEGylated emulsomes, ANOVA showed a significant difference in the entrapment efficiency among the formulation E12 (optimized emulsomes), E22, E23, and E24 (PEGylated VIN emulsomes) (P=0.004). Multiple comparisons Tukey's HSD revealed significant difference between optimized VIN emulsomes (E12) and each of the PEGylated emulsomes (E23 and E24), P=0.039, and 0.005, respectively. Also, there were statistical difference in EE between E22 and E24 (P=0.019). The higher drug entrapment of PEGylated emulsomes compared to the cationic emulsomes and optimized emulsomes (E12) could be credited to presence of PEG on the outer surface of emulsomes that increases the vesicle stability as well as decreases the drug leakage. Moreover, adding lipid MPEG-DSPE could result in increasing the amount of lipid in prepared emulsomes that lead to entrapment more lipophilic drug (VIN).

Figure 1A:
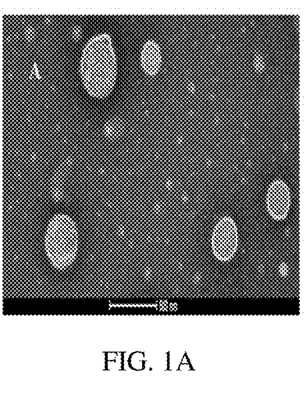
FIGS. 1A-C. Transmission Electron Microscope (TEM) of (A) VIN-emulsomes, (B) Cationic emulsomes, (C) PEGylated emulsomes with 22,500× magnification.
Figure 1B:
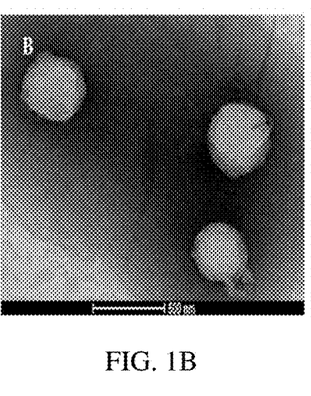
Figure 1C:
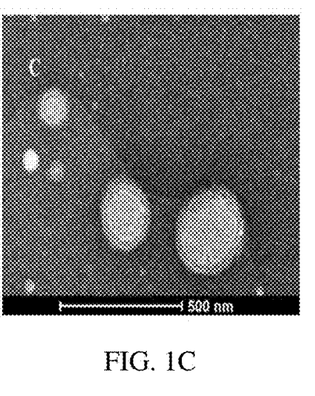
Figure 2A:
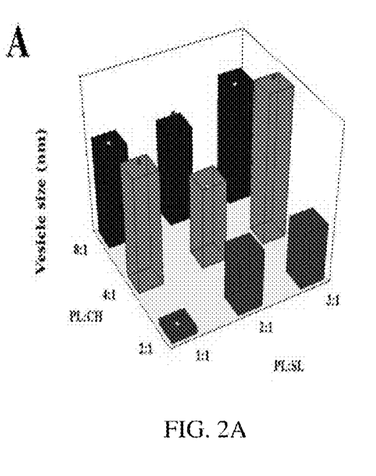
FIGS. 2A-D. Vehicle size response 3D plot for the effect of PL:SL ($X_1$), PL:CH ($X_2$), and SL type ($X_3$) on vesicle size ($Y_1$) of VIN emulsomes. A: SL type (Tripalmitin), B: SL type (Tristearin), C: PL:CH (4:1), D: PL:SL (2:1).
Figure 2B:
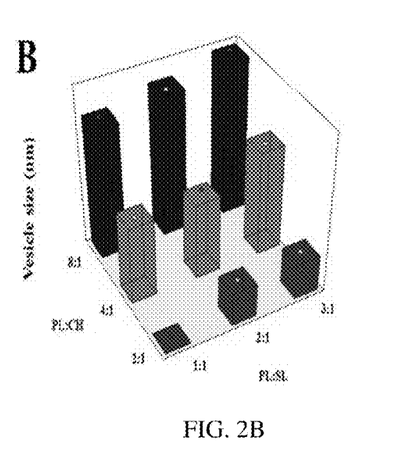
Figure 2C:
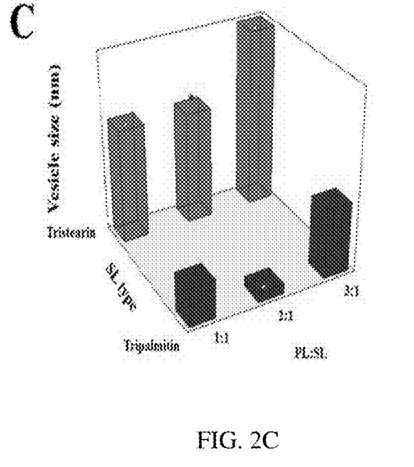
Figure 2D:
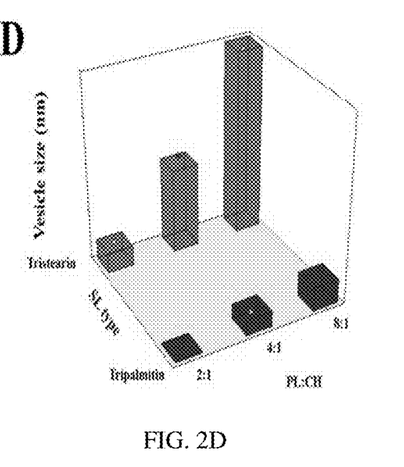
Figure 3A:
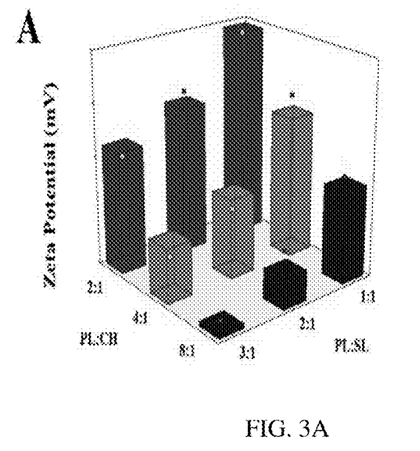
FIGS. 3A-D. Zeta potential 3D plot for the effect of PL:SL ($X_1$), PL: CH ($X_2$), and SL type ($X_3$) on zeta potential ($Y_2$) of VIN emulsomes. A: SL type (Tripalmitin), B: SL type (Tristearin), C: PL:CH (4:1), D: PL:SL (2:1)
Figure 3B:
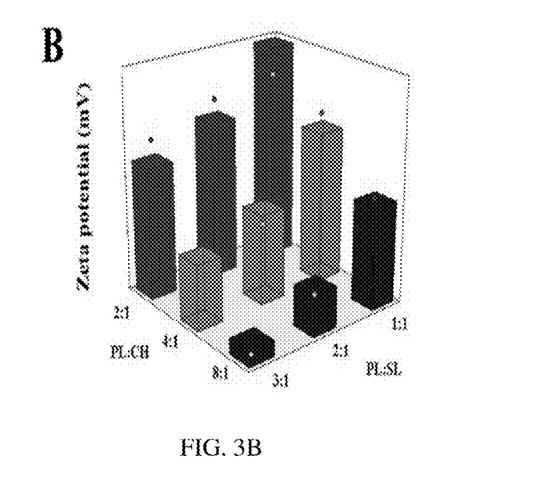
Figure 3C:
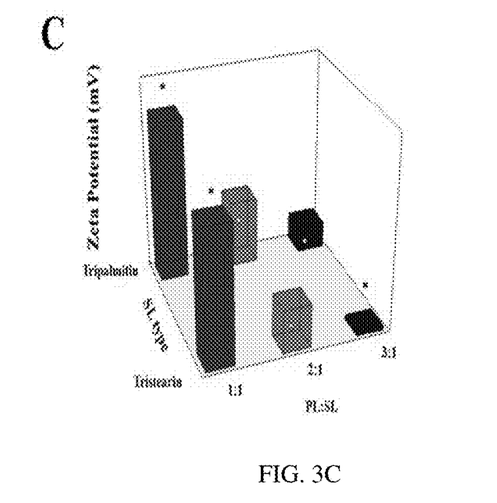
Figure 3D:
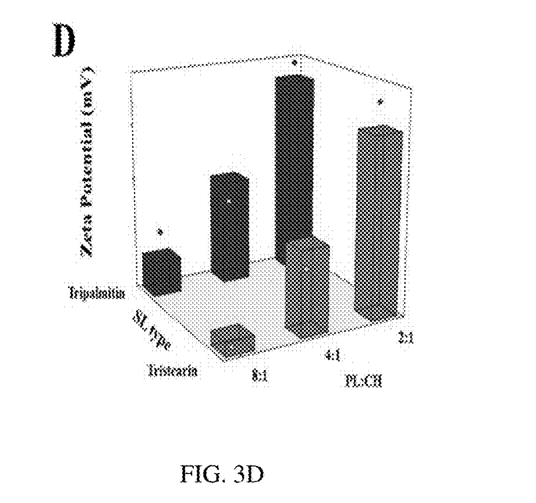
Figure 4A:
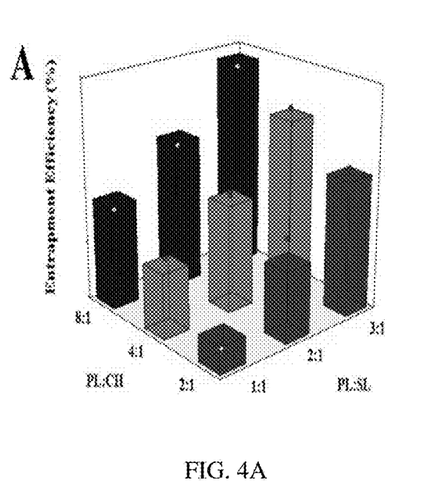
FIGS. 4A-D. Drug entrapment response 3D plot for the effect of PL:SL ($X_1$), PL:CH ($X_2$), and SL type ($X_3$) on entrapment efficiency ($Y_3$) of VIN emulsomes. A: SL type (Tripalmitin), B: SL type (Tristearin), C: PL:CH (4:1), D: PL:SL (2:1)
Figure 4B:
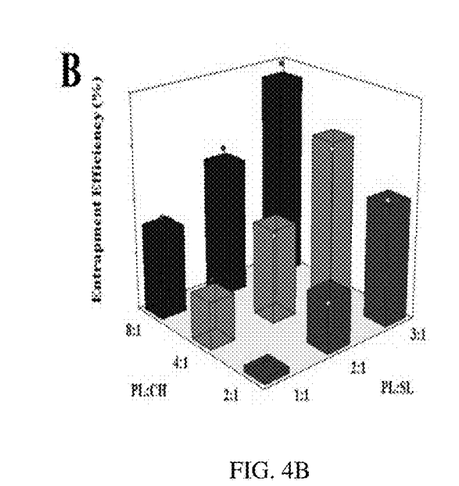
Figures 4C, 4D:
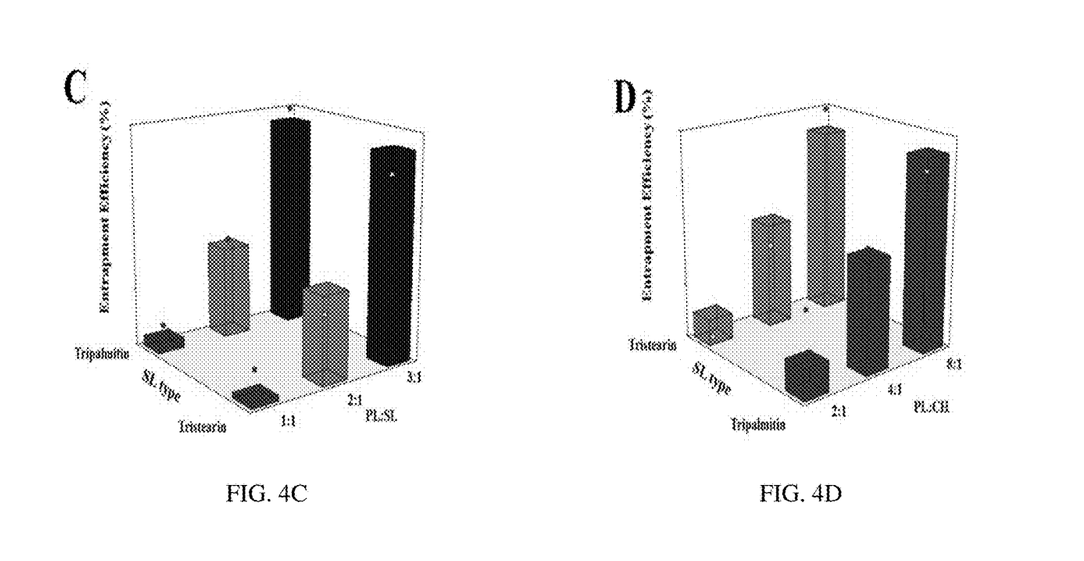
Figure 5A:
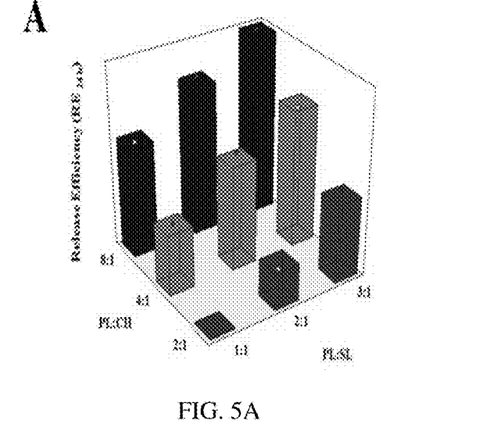
FIGS. 5A-D. Release efficiency response 3D plot for the effect of PL:SL ($X_1$), PL:CH ($X_2$), and SL type ($X_3$) on drug release after 24 h ($Y_4$) of VIN. A: SL type (Tripalmitin), B: SL type (Tristearin), C: PL:CH (4:1), D: PL:SL (2:1)
Figure 5B:
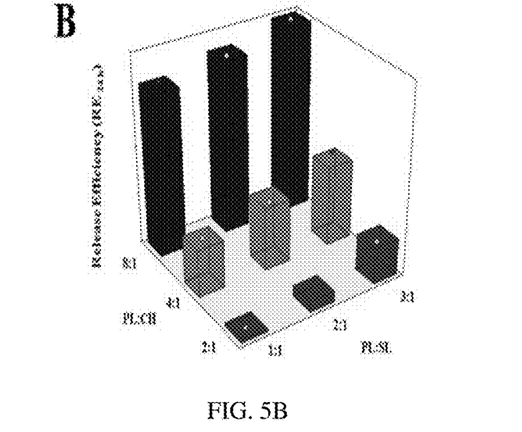
Figure 5C:
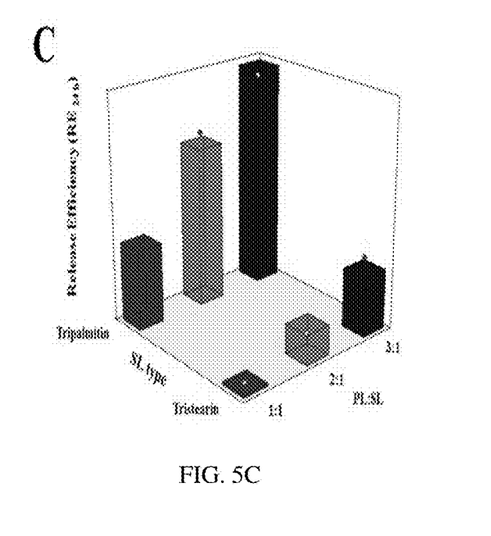
Figure 5D:
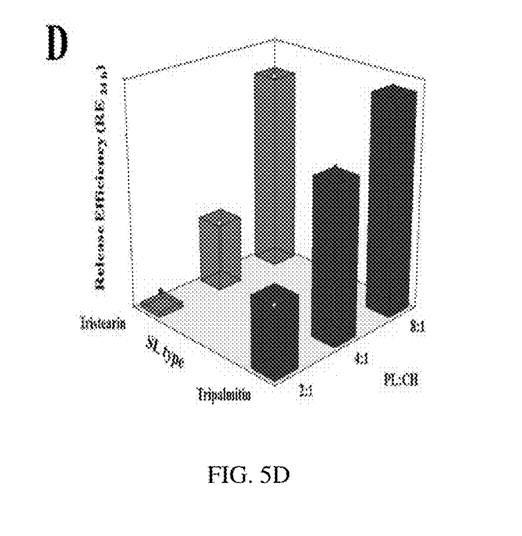
Figure 6A:
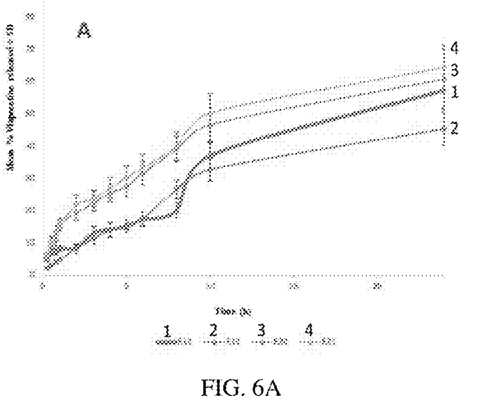
FIGS. 6A-B. Mean % Vinpocetine release profile (A) Cationic VIN emulsomes (B) PEGylated VIN emulsomes in phosphate buffer pH 6.8 at 35±0.5° C. (Results presented as mean±SD, n=3).
Figure 6B:
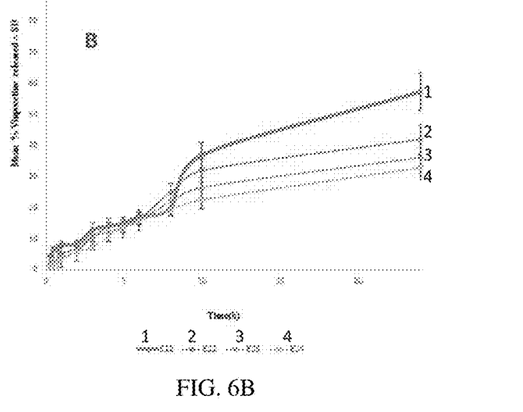

Addition of SA up to 0.25 molar ratio retarded the VIN release as shown in FIG. 6. ANOVA showed a significant difference in the in vitro release among the formulations E12 (optimized emulsomes), E19, E20, and E21 (cationic VIN emulsomes) (P=0.035). Multiple comparison Tukey's HSD test revealed no significant difference between each of optimized VIN emulsomes (E12) and of the cationic emulsomes. However, there was significant difference in the in vitro release between E19 and E21 (P=0.032). Retardation of drug release observed for positively charge emulsomes compared to negatively charged emulsomes (E12) could be ascribed to the electrostatic attraction between the negatively charged VIN and positively charged emulsomes. This interaction could lead to lower percentage of drug released. However, increase the molar ratio of SA above 0.25, resulted in fast drug release compared to the optimized formulation. This could be explained on the basis of incomplete solubility of SA in the hydration medium at higher concentration. Release efficiency after 24 hours of VIN from PEGylated emulsomes reported to be less than $RE_{24\ h}$ of optimized emulsomes (E12). ANOVA showed a significant difference in the in vitro release among the formulation E12 (optimized emulsomes), E22, E23, and E24 (PEGylated VIN emulsomes) (P=0.001). Multiple comparisons Tukey's HSD revealed significant difference between optimized VIN emulsomes (E12) and each of the PEGylated emulsomes (E22, E23, and E24), P=0.007, 0.003, and 0.000, respectively. However, there was no significant difference in the release upon using different concentration of MPEG-DSPE. Prolongation of release of VIN observed upon incorporation of MPEG-DSPE into the optimized emulsomes could be due to the effect of the added polymer in increasing the amount of total lipid, thus, increasing the entrapment of lipophilic VIN, as well as, controlling its release. The cationic (E19) and PEGylated (E24) VIN emulsomes attaining highest value of EE % and magnitude of zeta potential, and lowest vesicle size and release efficiency after 24 h were selected for in vivo studies.

Materials and Methods

Vesicle size is one of the main parameters that affect stability, encapsulation efficiency, drug release, biodistribution, as well as cellular uptake and permeation through BBB. Also, it contributes to the determination of clearance by the reticuloendothelial system (RES). As increasing the size of lipid nanocarier could lead to increase the uptake by the immune system cells. Furthermore, decreasing vesicle size resulted in increasing surface area available for drug absorption. The average vesicle size and zeta potential of VIN emulsomes were measured by dynamic light scattering (DLS) technique using Malvern particle size analyzer at 25±1° C. Emulsomes were diluted 50-100 folds before measurement. Average vesicle size and zeta potential was computed as a mean of six measurements.

The entrapment efficiency of VIN loaded emulsomes was determined by indirect method. To separate the unentrapped drug, 1 mL of VIN loaded emulsomal dispersion was ultracentrifuged at 100,000 rpm for 1 h at 4° C. The residue was washed twice with phosphate buffer (pH 6.8) and re-centrifuged again for 1 h. The combined supernatant was diluted with phosphate buffer (pH 6.8), and analyzed spectrophotometrically at λmax 273 nm [1,12,13]. all determinations were done in triplicate.

The entrapment efficiency was calculated using following equation:

$$EE\ \% = \left/ \frac{(Ct - Cu)}{Ct} \times 100 \right.$$

Where Ct represents the amount of total drug; and Cu represents the amount of unentrapped drug.

Glass basket dialysis technique was applied to study in vitro release using modified USP dissolution apparatus[8]. Samples of emulsomal dispersions (equivalent to 0.5 mg of VIN) were placed inside glass cylinder tube (2.5 cm in diameter and 7.5 cm in length). Each tube was tightly covered with previously soaked dialysis membrane (MWCO12,000-14,000 Da) at one end, while the other end was attached to the USP dissolution apparatus shaft instead of basket. The shaft was then lowered to the dissolution vessel containing 200 mL phosphate buffer (pH 6.8). The temperature was kept constant at 35±0.5° C. and the rotation speed was set at 50 rpm in order to mimic the low mixing condition of nose. The vessels were covered during the test to minimize evaporation of the release medium. Aliquots were withdrawn at predetermined time intervals of 0.25, 0.5, 0.75, 1, 2, 3, 4, 5, 6, 8, 10, and 24 h. The amount of VIN released was assayed using HPLC method. All experiments were done in triplicate.

The effect of formulation parameters was studied using $3^2 2^1$ full factorial design. Three formulation parameters namely; PL:SL weight ratio ($X_1$), PL:CH molar ratio ($X_2$), and solid lipid type ($X_3$), were selected as independent variables. The quantitative variables $X_1$ and $X_2$ were studied at three levels, (1:1, 2:1, and 3:1) for $X_1$, (2:1, 4:1, and 8:1) for $X_2$. While the qualitative variables $X_3$ was studied at two levels (TS and TP). The design yielded 18 experimental runs. The effects of the independent variables ($X_1$, $X_2$, and $X_3$) on the responses including vesicle size ($Y_1$), zeta potential ($Y_2$), entrapment efficiency ($Y_3$), and release efficiency after 24 h ($Y_4$) were analyzed using Design-Expert software (version 11; Stat-Ease, Inc., Minneapolis, Minn., USA, 2018). The model maximizing both adjusted and predicted determination coefficients ($R^2$) and minimizing sum of squares (PRESS) was selected for each response. Analysis of variance ANOVA was applied to determine the significance of the studied factors and interaction between them at P-value≤0.05. Furthermore, the desirability function was applied in order to determine the optimized VIN emulsomes. The composition of optimized emulsomes was selected based on minimized vesicle size, and release efficiency after 24 h ($RE_{24\ h}$), and maximized absolute value of zeta potential, and entrapment efficiency (EE %).

Example 2. In Vivo Pharmacokinetic Analysis of VIN Brain Targeted Emulsomes

In Vivo Pharmacokinetic Analysis of VIN Brain Targeted Emulsomes

Evaluation of in vivo pharmacokinetic performance of the selected VIN emulsomes was assessed in rats compared to the oral market product. The VIN concentrations spiked in plasma exhibited linear correlation with the peak area ratio of VIN/InSt. (VIN concentration versus relative peak area of VIN/InSt). The linearity was verified with a regression coefficient (R) 0.9914. The regression equation of the best fitting line representing the calibration curve was computed as y=0.0021X. Plasma samples showed that the percentage of extraction recovery was 99±1.3%.

Pharmacokinetic of VIN in Plasma

Figure 7A:
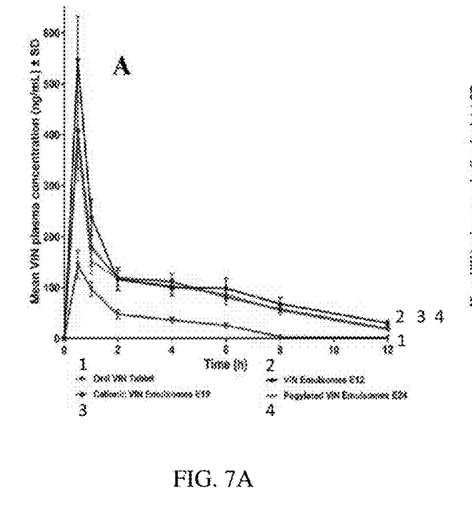
FIGS. 7A-B. (A) Mean plasma concentrations, (B) Brain concentrations versus time of VIN in rats after intranasal administration of VIN optimized emulsome (E12), cationic emulsomes (E19), PEGylated emulsomes (E24) compared to reference oral tablet. Data presented as mean±SD (n=6).

The mean plasma concentrations of VIN versus time following intranasal instillation of optimized VIN emulsomes (E12), cationic emulsomes (E19), PEGylated emulsomes (E24) compared to oral market product are graphically illustrated in FIG. 7A. ANOVA revealed statistical significant difference in maximum plasma concentration ($C_{max}$), plasma $AUC_{(0-12)}$ and $AUC_{(0-\infty)}$ among the tested formulations, (P<0.0001). The results indicate that VIN achieved higher level in plasma following nasal administration of VIN emulsomes compared to oral administration of tablets.

Tukey's HSD Multiple comparison revealed that the $C_{max}$, $AUC_{(0-12)}$, and $AUC_{(0-\infty)}$ of VIN were significantly higher following nasal instillation of optimized emulsomes (E12) compared with oral VIN, (P<0.0001). Regarding time to reach maximum plasma concentration ($T_{max}$), E12 reached its maximum plasma concentration after median time of 0.5 hr, while oral market VIN reached after 1 h. However, Kruskal-Wallis test revealed no statistical difference among $T_{max}$ (P=0.467). The aforementioned findings could be attributed to the high blood supply of the nasal cavity, that could allow rapid absorption of VIN compared to oral route. Moreover, intranasal route avoids first pass metabolism leading to enhanced bioavailability of the drug compared to oral route (VIN hepatic metabolism ~75%)[9].

Furthermore, Tukey's HSD Multiple comparison revealed that the cationic emulsomes (E19) and PEGylated emulsomes (E24) showed significantly higher $C_{max}$, $AUC_{(0-12)}$ and $AUC_{(0-\infty)}$ compared to the oral market product (P≤0.05). However, both cationic and PEGylated emulsomes exhibited significant lower $C_{max}$, $AUC_{(0-12)}$ and $AUC_{(0-\infty)}$ than optimized emulsomes (E12), suggesting that the surface modified optimized emulsomes (E19 and E24) could improve availability of VIN in the brain rather than plasma, (P≤0.05).

Pharmacokinetic of VIN in Brain Tissue

Figure 7B:
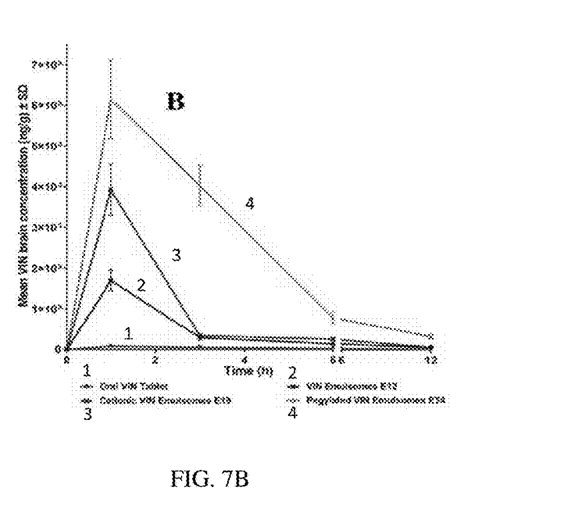

The mean brain concentrations of VIN versus time following intranasal instillation of optimized VIN emulsomes (E12), cationic emulsomes (E19), PEGylated emulsomes (E24) compared to oral VIN administration are graphically illustrated in FIG. 7B. ANOVA revealed statistical significant difference in $C_{max}$, $AUC_{(0-12)}$ and $AUC_{(0-\infty)}$ among the tested formulations, (P<0.0001). Tukey's HSD Multiple comparison revealed that the $C_{max}$, $AUC_{(0-12)}$, and $AUC_{(0-\infty)}$ of VIN were significantly higher following nasal instillation of optimized emulsomes (E12) compared with oral VIN, (P≤0.05). However, Kruskal-Wallis test revealed no statistical difference among $T_{max}$ (P=0.591). The higher levels of VIN achieved in brain following nasal administration of VIN emulsomes compared to oral administration of tablets could be explained by the uptake of VIN emulsomes via two different mechanisms, either by systemic or olfactory pathway. In systemic pathway, some of the drug is absorbed directly into the systemic circulation by avoiding first pass metabolism unlike oral administration. While in the olfactory pathway, drug uptake from olfactory region in the nasal cavity directly into cerebrospinal fluid and brain tissue. In the brain, the olfactory bulb is projected at various regions such as the amygdala, piriform cortex, and hypothalamus, thus enabling the direct drug delivery from the nasal cavity to the brain[10][11]. In addition, emulsomes formulations improved the drug bioavailability, due to the ability of emulsomal system to encapsulate the lipophilic molecules and protect them from fast excretion. Additionally, emulsomes are lipid rich formulation, it composed of phospholipid and solid lipid (3:1 PL:SL) that enhanced drug permeation into systemic circulation. Thus, the high lipophilicity increased affinity of VIN to permeate the BBB[12][13].

Tukey's HSD Multiple comparison revealed that the cationic VIN emulsomes (E19) exhibited markedly higher VIN concentration compared to oral product. Mean AUC of cationic emulsomes was around 20-fold higher than oral VIN. This could be ascribed to the attractive forces between positively charged emulsomes and negatively charged BBB that allow higher uptake of cationic emulsomes into the brain. The nasal administration of PEGylated emulsomes (E24) exhibited higher VIN concentration than the corresponding oral VIN tablets. Significant difference was observed in $C_{max}$, $AUC_{(0-12)}$, and $AUC_{(0-\infty)}$ based on Tukey's HSD test (P<0.0001). On the basis of in vivo data, result indicated that the PEGylating increased brain targeting effect than both oral and optimized emulsomes (E12). Glucose transporters (GLUTs) considered as one of carrier-mediated transporter, which responsible for transporting glucose into or out of the brain to sustain the cerebral function. GLUTs are highly expressed in the brain capillary endothelial cells. PEG considered as a ligand with high affinity binding to the GLUT1 therefore, it enhances the brain targeting of prepared emulsomes.

It was found that both cationic and PEGylated emulsomes had 3-4 fold higher in $C_{max}$, compared to the optimized emulsomes (E12). The difference in $C_{max}$ was significant between optimized VIN emulsomes (E12) and each of the cationic and PEGylated emulsomes (E19 and E24, respectively), (P≤0.05). This study confirmed that intranasal instillation of surface modified optimized emulsomes achieved better brain targeting compared to the oral market product and optimized emulsomes. PEG, target brain endothelial cells receptors by inducing receptor-mediated transcytosis, while SA interact with negative charges present at the BBB, leading to that adsorptive-mediated endocytosis. Beside that cationic emulsomes had high affinity to the negatively charged BBB, thus enhancing the brain targeting. The in vivo study in the present work proved the ability of emulsomal system to improve VIN brain delivery.

CONCLUSIONS

This work demonstrated that intranasal VIN loaded emulsomes was successful in improving the brain delivery of VIN. The results showed superiority of brain targeting effect of optimized VIN emulsomes, cationic, and PEGylated emulsomes than VIN oral market product. The superiority of results could be due to nanosized emulsomes, high zeta potential, high drug entrapment efficiency, and retarded drug release from prepared emulsomes. In vivo studies revealed that $C_{max}$ and AUC of prepared emulsomes were significantly higher when compared with oral VIN. As a conclusion, this formulation represents a good alternative for oral VIN.

ACKNOWLEDGEMENT

The Deanship of Scientific Research (DSR) at King Abdulaziz University, Jeddah, funded this project under grant no. (RG-13-166-40).

REFERENCES

Throughout this application, various references describe the state of the art to which this disclosure pertains. The disclosures of these references are hereby incorporated by reference into the present disclosure.

1 Abbott, N. J. Blood-brain barrier structure and function and the challenges for CNS drug delivery. *J Inherit Metab Dis* 36, 437-449, doi:10.1007/s10545-013-9608-0 (2013).

2 El-Zaafarany, G. M., Soliman, M. E., Mansour, S. & Awad, G. A. Identifying lipidic emulsomes for improved oxcarbazepine brain targeting: In vitro and rat in vivo studies. *Int J Pharm* 503, 127-140, doi:10.1016/j.ijpharm.2016.02.038 (2016).

3 Paliwal, R., Paliwal, S. R., Mishra, N., Mehta, A. & Vyas, S. P. Engineered chylomicron mimicking carrier emulsome for lymph targeted oral delivery of methotrexate. *Int J Pharm* 380, 181-188, doi:10.1016/j.ijpharm.2009.06.026 (2009).

4 Nageeb El-Helaly, S., Abd Elbary, A., Kassem, M. A. & El-Nabarawi, M. A. Electrosteric stealth Rivastigmine loaded liposomes for brain targeting: preparation, characterization, ex vivo, bio-distribution and in vivo pharmacokinetic studies. *Drug Deliv* 24, 692-700, doi: 10.1080/10717544.2017.1309476 (2017).

Zhou, X. & Chen, Z. Preparation and performance evaluation of emulsomes as a drug delivery system for silybin. *Arch Pharm Res* 38, 2193-2200, doi:10.1007/s12272-015-0630-7 (2015).

6 El-Nesr, O. H., Yahiya, S. A. & El-Gazayerly, O. N. Effect of formulation design and freeze-drying on properties of fluconazole multilamellar liposomes. *Saudi Pharm J* 18, 217-224, doi:10.1016/j.jsps.2010.07.003 (2010).

7 Narayan, R. et al. Development of risperidone liposomes for brain targeting through intranasal route. *Life Sci* 163, 38-45, doi:10.1016/j.lfs.2016.08.033 (2016).

8 El-Laithy, H. M., Shoukry, O. & Mahran, L. G. Novel sugar esters proniosomes for transdermal delivery of vinpocetine: preclinical and clinical studies. *Eur J Pharm Biopharm* 77, 43-55, doi:10.1016/j.ejpb.2010.10.011 (2011).

9 Ahirrao, M. & Shrotriya, S. In vitro and in vivo evaluation of cubosomal in situ nasal gel containing resveratrol for brain targeting. *Drug Dev Ind Pharm* 43, 1686-1693, doi:10.1080/03639045.2017.1338721 (2017).

Arumugam, K. et al. A study of rivastigmine liposomes for delivery into the brain through intranasal route. *Acta Pharm* 58, 287-297, doi:10.2478/v10007-008-0014-3 (2008).

11 Liu, S. & Ho, P. C. Intranasal administration of brain-targeted HP-beta-CD/chitosan nanoparticles for delivery of scutellarin, a compound with protective effect in cerebral ischaemia. *J Pharm Pharmacol* 69, 1495-1501, doi: 10.1111/jphp.12797 (2017).

12 Xie, F. et al. Investigation of glucose-modified liposomes using polyethylene glycols with different chain lengths as the linkers for brain targeting. *Int J Nanomedicine* 7, 163-175, doi:10.2147/IJN.S23771 (2012).

13 Vieira, D. B. & Gamarra, L. F. Getting into the brain: liposome-based strategies for effective drug delivery across the blood-brain barrier. *Int J Nanomedicine* 11, 5381-5414, doi:10.2147/IJN.S117210 (2016).

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

The invention claimed is:

1. An emulsome composition, comprising
phosphatidylcholine;
cholesterol;
tristearin; and
vinpocetine,
wherein a surface of the emulsome is modified with stearylamine or with [N-(carbonyl-methoxypropylethyleneglycol-2000)-1,2-distearoyl-sn-glycero-3-phosphoethanolamine, sodium salt] (MPEG-DSPE),
wherein a weight ratio of phosphatidylcholine to tristearin is from 3.5:1 to 2.5:1, and wherein a molar ratio of phosphatidylcholine to cholesterol is from 2.5:1 to 1.5:1.

2. The emulsome composition of claim 1, wherein the surface of the emulsome is modified with MPEG-DSPE.

3. The emulsome composition of claim 1, wherein the surface of the emulsome is modified with stearylamine.

4. The emulsome composition of claim 1, wherein the weight ratio of phosphatidylcholine to tristearin is 3:1, and wherein the molar ratio of phosphatidylcholine to cholesterol is 2:1.

* * * * *